United States Patent [19]

Gottlob et al.

[11] 4,415,243

[45] Nov. 15, 1983

[54] OPTICAL TEST CHART FOR TESTING BINOCULAR READING ABILITY

[75] Inventors: Heinz Gottlob, Königsbronn; Horst Falk, Aalen, both of Fed. Rep. of Germany

[73] Assignee: Carl-Zeiss-Stiftung, Heidenheim, Fed. Rep. of Germany

[21] Appl. No.: 331,909

[22] Filed: Dec. 18, 1981

[30] Foreign Application Priority Data

Feb. 20, 1981 [DE] Fed. Rep. of Germany ... 8104761[U]

[51] Int. Cl.³ .......................... A61B 3/08; A61B 3/02
[52] U.S. Cl. .................................... 351/201; 351/232; 351/240
[58] Field of Search ............... 351/201, 202, 232, 240, 351/239, 243

[56] References Cited

U.S. PATENT DOCUMENTS 2,294,382  9/1942  Burian .................................. 351/201

*Primary Examiner*—John K. Corbin
*Assistant Examiner*—Rodney B. Bovernick
*Attorney, Agent, or Firm*—Stonebraker, Shepard & Stephens

[57] ABSTRACT

An optical test chart for testing binocular vision. The chart has three lines of text, with the middle line printed or marked in letters or characters which have no polarizing effect. The line above this middle line is marked in letters or characters which have the effect of polarizing light reflected from them, in a plane of polarization in one direction, while the line below the middle line is similarly marked with letters or characters having the effect of polarizing reflected light but with the plane of polarization in a different direction at a substantial angle, preferably a right angle, to the direction of polarization caused by the upper line. The person whose vision is being tested views the test chart through polarizing spectacles, the spectacle in front of one eye having a plane of polarization corresponding to that of the upper line of text on the chart, and the spectacle in front of the other eye having a plane of polarization corresponding to that of the lower line of the text. If the person being tested perceives all three lines of the text with equal contrast, he has normal binocular vision or reading ability. If he perceives a difference in contrast between the different lines on the chart, or if he is unable to read either the top or bottom line, his binocular reading ability is impaired, and the kind of impairment can be determined by determining what he is able to read. Preferably a series of such test charts with the text in letters of different size are mounted displaceably on a lectern or easel, so that the chart sheets may be selectively turned to test the subject with lettering of different size, to determine the minimum size which the subject can read, thus establishing his visual acuity as well as his binocular reading ability.

7 Claims, 4 Drawing Figures

OPTICAL TEST CHART FOR TESTING BINOCULAR READING ABILITY

BACKGROUND OF THE INVENTION

The present invention relates to an optical test chart for testing binocular reading ability. Polarization filters having directions of vibration crossed with respect to each other are arranged in front of the eyes of the test subject, and through these, the subject views the test chart containing polarized indicia.

Optical test charts are known which contain figures composed of two parts, the different parts of the figures being formed with polarizing action with directions of polarization extending crosswise with respect to each other. The test subject therefore sees only a part of the figures with each eye. With normal binocular reading ability these two optically separate visual impressions appear to the test subject as a single figure.

Optical test charts are also known which contain two or more letters in each of two horizontal lines. The letters of each line have polarizing action with directions of polarization extending crosswise with respect to each other and are arranged in such a manner that letters which stand next to each other horizontally or one above the other vertically have directions of polarization which are crossed relative to each other. The test subject therefore sees four or five letters in the case of normal vision.

All of these optical test charts require a certain concentration on the part of the test subject since he must describe the picture seen by him. The examiner can draw his conclusions only from the description given to him by the person being tested.

SUMMARY OF THE INVENTION

The object of the present invention is to provide an optical test chart for the testing of binocular reading ability which makes it possible immediately for the examiner to known whether there is binocular reading ability on the part of the test subject, and which furthermore permits a testing of visual acuity.

This object is achieved by providing an optical test chart which includes several sheets having lines of letters of different size on different sheets, the sheets being arranged in inter-changeable manner on a support; and on each sheet at least one line formed of polarizing letters is arranged above and below a first line formed of letters of non-polarizing action; and the directions of polarization in the lines lying above and below the first line are crossed with respect to each other.

It is particularly advantageous to impart a uniform direction of polarization to all letters of the same line. However, it is also possible to develop the lines in such a manner that successive letters in the same line have crossed directions of polarization.

In this optical test chart, the middle line is perceived by both eyes of the test subject. It therefore serves as a locking means which fixes the eyes of the test subject on the text. If all lines are seen with the same contrast by the test subject there is then correct binocular reading ability. This ability is disturbed if the lines of the text are perceived with different contrast; it is no longer present when the test subject perceives only half the text in addition to the middle line.

The lines of letters advisedly represent a continuous text so that the examiner can immediately note from the text read aloud by the test subject whether or not binocular viewing and reading ability are present.

The letters of several sheets can be formed of different printing type and the text to be read can be of any desired content or language.

The new optical test chart is particularly well suited for the testing of near vision. It is possible in a simple manner, by replacing the sheets, to show the test subject letters of different size and thereby determine the minimum size of letter on the text that can be read. In addition, it is possible to check whether and how the two eyes participate in the reading.

For near-vision testing, the optical test chart is advisedly developed in such a manner that the sheets which bear the lines of letters or text are arranged so that they can be turned over on a support developed as a lectern which has at least one side with an oblique surface which is suitable for near vision reading.

The new optical test chart can be used to particular advantage to determine to what extent binocular vision can be obtained in persons with impaired sight by means of magnifying aids in vision of any desired kind, for instance binocular loupes.

BRIEF DESCRIPTION OF THE DRAWINGS

The invention will be explained below in further detail with reference to the accompanying drawings, in which.

DESCRIPTION OF THE PREFERRED EMBODIMENT

Figure 1:
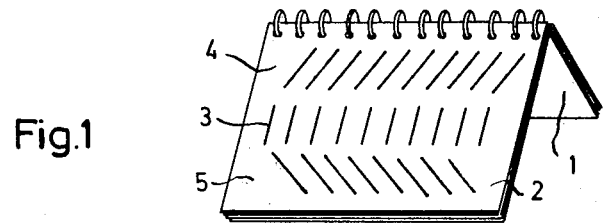
FIG. 1 is a schematic diagram of one embodiment of the invention.

In FIG. 1, 1 is a support developed as a lectern which bears a plurality of sheets 2 adapted to be turned to bring any desired one of the sheets into reading position. The visible uppermost sheet 2 contains three lines of lettering or text, indicated schematically at 3, 4, and 5, on a white background. The center line 3 consists of non-polarizing letters while lines 4 and 5 consist of polarizing letters which are produced, for instance, by a printing process or by means of photo-techniques. The oblique strokes representing the text of lines 4 and 5 schematically indicate polarization, and it will be noted that the direction of polarization of line 4 is crosswise with respect to the direction of polarization of line 5.

It is also possible to develop lines 4 and 5 in such a manner that successive letters in one line have crossed directions of polarization, but the preferred construction is to have all the letters of each line polarized in the same direction.

In front of the eyes 6, 7 of the test subject there are arranged polarization filters 8,9 which have directions of vibration which are crossed with respect to each other. Thus, in the example shown the test subject with his left eye 6 sees only lines 3 and 4, because the directions of vibration of the letters in line 3 and the polatization filter 8 are crossed and these letters therefore appear black against the white background, while the black letters in line 4 are non-polarizing and appear also black. The right eye 7 can not perceive the letters in line 3, because the directions of vibration of these letters and the polarization filter 9 are parallel and the letters therefore appear white against the white background. The right eye 7 can, however, perceive the letters in lines 4 and 5.

If the binocular reading ability of the test subject is unimpaired, he sees the letter or text lines 3, 4, and 5 with both eyes and with the same contrast. These lines of letters represent a coherent text so that the examiner can rapidly and in simple manner establish whether the test subject who reads aloud the text observed is viewing with binocular vision.

In the embodiment shown in the drawing the lectern-shaped support 1 is developed in such a manner that the surface thereof which bears the visible sheets 2 has an oblique position which is suitable for near viewing.

The sheets 2 are fastened to the support 1 in such a manner that they can be turned thereon, and successive sheets contain lines of letters of different size. In that way it is easy to determine, by placing different sheets in reading position, what is the minimum size of the text that can be read by the text subject.

Figure 2:
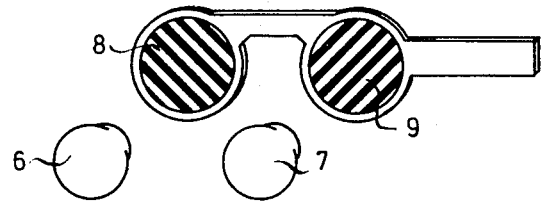
FIG. 2 is a face view of the monocular visual impression for the left eye.
Figure 2:
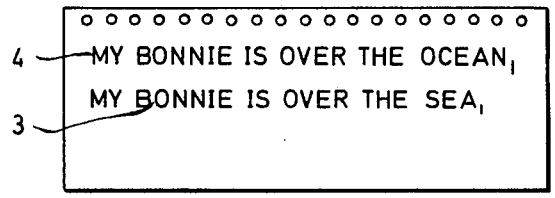
Figure 3:
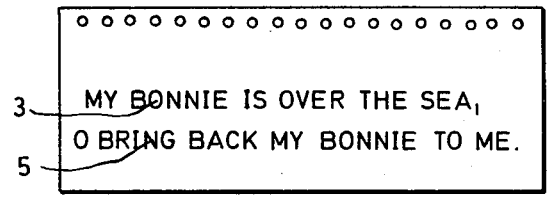
FIG. 3 is a similar view of the monocular visual impression for the right eye.
Figure 4:
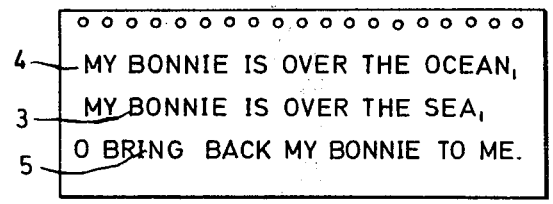
FIG. 4 is a similar view illustrating the visual impression in the case of binocular vision.

FIG. 2 shows the monocular visual impression for the left eye 6 of the test subject, which perceives the coherent text in lines 3 and 4. FIG. 3 shows the monocular visual impression of the right eye; in this case the lines 3 and 5 are observed. In case of binocular vision, the picture shown in FIG. 4 is observed which consists of the lines 3, 4, and 5, and reproduces the entire text.

What is claimed is:

1. An optical test chart for testing binocular reading ability for the viewing of which polarization filters with oppositely crossed directions of vibration are arranged in front of the eyes of a test subject, characterized by the fact that a plurality of sheets (2) bearing lines of letters of different size are arranged interchangeably on a support (1); that at least one line (4, 5) formed of polarizing letters is arranged on each sheet (2) above and below a first line (3) formed of non-polarizing letters; and that the directions of polarization in the lines (4, 5) lying above and below the first line (3) are crossed with respect to each other.

2. The invention defined in claim 1, wherein the letters of any one polarized line (4 or 5) have the same direction of polarization.

3. The invention defined in claim 1, wherein successive letters in each of the lines (4, 5) formed of polarizing letters have crossed directions of polarization.

4. The invention defined in claim 2, wherein the sheets (2) are arranged in turntable manner on a support (1).

5. The invention defined in claim 4, wherein said support (1) is developed as a lectern which has at least one surface which has an oblique position which is suitable for near vision.

6. The invention defined in claim 3, wherein the sheets (2) are arranged in turntable manner on a support (1).

7. The invention defined in claim 6, wherein said support (1) is developed as a lectern which has at least one surface which has an oblique position which is suitable for near vision.

* * * * *